United States Patent
Bradley

(10) Patent No.: US 9,511,229 B2
(45) Date of Patent: Dec. 6, 2016

(54) SYSTEM AND METHOD FOR USING IMPEDANCE TO DETERMINE PROXIMITY AND ORIENTATION OF SEGMENTED ELECTRODES

(75) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1147 days.

(21) Appl. No.: 13/533,532

(22) Filed: Jun. 26, 2012

(65) Prior Publication Data

US 2013/0006324 A1    Jan. 3, 2013

Related U.S. Application Data

(60) Provisional application No. 61/502,192, filed on Jun. 28, 2011.

(51) Int. Cl.
| | |
|---|---|
| *A61N 1/36* | (2006.01) |
| *A61N 1/05* | (2006.01) |
| *A61B 5/053* | (2006.01) |
| *A61N 1/08* | (2006.01) |
| *A61B 5/06* | (2006.01) |

(52) U.S. Cl.
CPC ......... *A61N 1/36125* (2013.01); *A61N 1/0551* (2013.01); *A61B 5/0538* (2013.01); *A61B 5/06* (2013.01); *A61N 1/08* (2013.01); *A61N 1/36182* (2013.01)

(58) Field of Classification Search
CPC .... A61N 1/3605; A61N 1/36021; A61N 1/05; A61N 1/0551
USPC ............... 607/45, 46, 62, 116, 117
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |

(Continued)

OTHER PUBLICATIONS

PCT International Preliminary Report on Patentability (Chapter I of the Patent Cooperation Treaty) for PCT/US2012/044238, Applicant: Boston Scientific Neuromodulation Corporation, Form PCT/IB/326 and 373, dated Jan. 16, 2014 (8pages).

(Continued)

*Primary Examiner* — Christopher D Koharski
*Assistant Examiner* — Roland Dinga
(74) *Attorney, Agent, or Firm* — Schwegman Lundberg & Woessner, P.A.

(57) ABSTRACT

A method for implanting a neurostimulation lead within a patient includes measuring impedances of electrodes on the lead in order to correctly position the lead relative to a target tissue region. The electrodes are circumferentially segmented electrodes that are spaced from each other about the longitudinal axis of the lead. When the difference between the impedances of the electrodes exceeds a threshold value, the lead is in the correct position. In accordance with another embodiment, impedance measurements are used to select which one of the electrodes is closest to the target tissue region. By determining which electrode has the highest impedance and which electrode has the lowest impedance, the type of tissue adjacent to each electrode can be determined based on the conductivity properties of the tissue. The target tissue region may be a spinal cord, a posterior longitudinal ligament, white matter, or gray matter.

23 Claims, 10 Drawing Sheets

(56) References Cited

U.S. PATENT DOCUMENTS

| | | | |
|---|---|---|---|
| 7,317,948 B1 | 1/2008 | King et al. | |
| 7,650,184 B2 | 1/2010 | Walter | |
| 8,019,439 B2 | 9/2011 | Kuzma et al. | |
| 2003/0139781 A1* | 7/2003 | Bradley | A61N 1/08 607/48 |
| 2007/0168004 A1 | 7/2007 | Walter | |
| 2007/0168007 A1 | 7/2007 | Kuzma et al. | |
| 2007/0203537 A1* | 8/2007 | Goetz | A61N 1/0529 607/59 |
| 2007/0208394 A1 | 9/2007 | King et al. | |
| 2010/0268298 A1* | 10/2010 | Moffitt | A61N 1/0534 607/45 |
| 2011/0009927 A1 | 1/2011 | Parker et al. | |

OTHER PUBLICATIONS

U.S. Appl. No. 61/427,441, Neurostimulation System for Selectively Estimating Volume of Activation and Providing Therapy, Inventor: Michael A. Moffitt, filed Dec. 27, 2010.

PCT International Search Report for PCT/US2012/044238, Applicant: Boston Scientific Neuromodulation Corporation, Form PCT/ISA/210 and 220, dated Dec. 5, 2012 (6pages).

PCT Written Opinion of the International Search Authority for PCT/US2012/044238, Applicant: Boston Scientific Neuromodulation Corporation, Form PCT/ISA/237, dated Dec. 5, 2012 (6pages).

* cited by examiner

SYSTEM AND METHOD FOR USING IMPEDANCE TO DETERMINE PROXIMITY AND ORIENTATION OF SEGMENTED ELECTRODES

RELATED APPLICATION DATA

The present application claims the benefit under 35 U.S.C. §119 to U.S. provisional patent application Ser. No. 61/502,192, filed Jun. 28, 2011. The foregoing application is hereby incorporated by reference into the present application in its entirety.

FIELD OF THE INVENTION

The present inventions relate to tissue stimulation systems, and more particularly, to systems and methods for determining proximity and orientation of segmented stimulation electrodes relative to target tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, peripheral vascular disease, and angina pectoralis, and the application of tissue stimulation has begun to expand to additional applications such as heart failure and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. A typical stimulation parameter set may include the electrodes that are acting as anodes or cathodes, as well as the amplitude, duration, and rate of the stimulation pulses. The RC may, itself, be programmed by a clinician, for example, by using a clinician's programmer (CP), which typically includes a general purpose computer, such as a laptop, with a programming software package installed thereon. Typically, the RC can only control the neurostimulator in a limited manner (e.g., by only selecting a program or adjusting the pulse amplitude or pulse width), whereas the CP can be used to control all of the stimulation parameters, including which electrodes are cathodes or anodes.

In the context of an SCS procedure, one or more neurostimulation leads are introduced through the patient's back into the epidural space, such that the electrodes carried by the leads are arranged in a desired pattern and spacing to create an electrode array. One type of commercially available neurostimulation lead is a percutaneous lead, which can be introduced proximal to the affected spinal tissue through a Touhy-like needle, which passes through the skin, between the desired vertebrae, and is positioned epidurally. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the spinal cord. After proper placement of the neurostimulation leads at the target area of the spinal cord, the leads are anchored in place at an exit site to prevent movement of the neurostimulation leads. To facilitate the location of the neurostimulator away from the exit point of the neurostimulation leads, lead extensions are sometimes used.

The neurostimulation leads, or the lead extensions, are then connected to the IPG, which can then be operated to generate electrical pulses that are delivered, through the electrodes, to the targeted tissue. In the particular case of traditional stimulation treatment of chronic pain, this tissue is typically the dorsal column and dorsal root fibers within the spinal cord. Such stimulation creates the sensation known as paresthesia, which can be characterized as an alternative sensation that reduces the pain signals sensed by the patient. Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy, and as such, precise positioning of the leads proximal to the targets of stimulation is critical to the success of the therapy.

However, percutaneous leads are typically implanted near target tissue using a "blind" needle approach. Imaging tools may be used to assist in correctly placing the leads near the target tissue, but imaging tools may be imprecise in terms of guiding placement. For example, because soft tissue is not shown in an x-ray, only the position of the lead relative to the vertebral bones of the spinal column is shown in an x-ray. Therefore, it is almost impossible to tell how close the lead is to the dura of the spinal cord when looking at an x-ray. Additionally, if the electrodes on the leads are segmented circumferential electrodes (e.g., as described in U.S. Provisional Patent Application Ser. No. 61/427,441, which is expressly incorporated herein by reference), the orientation of the electrodes intended for applying stimulation to the targets may not be known or controlled.

There, thus, remains a need for a system and method for precisely determining the location and orientation of segmented circumferential electrodes relative to target tissue.

SUMMARY OF THE INVENTION

Each of the methods described below uses a neurostimulation lead having a longitudinal axis and an electrode ring segmented into at least two electrodes circumferentially spaced from each other about the longitudinal axis. The at least two electrodes may be diametrically disposed from each other. Each of the systems described below are for use with the neurostimulation lead, as described above, positioned relative to a target tissue region.

In accordance with a first aspect of the present inventions, a method for of performing a medical procedure on a patient is provided. The method includes positioning the neurostimulation lead within the patient relative to a target tissue region. The target tissue region may be a spinal cord, a posterior longitudinal ligament, white matter, or gray matter. For example, positioning the neurostimulation lead within the patient may include positioning the neurostimulation lead in an epidural space such that the target tissue region is the spinal cord. In another example, positioning the neurostimulation lead within the patient may include positioning the neurostimulation lead in a ventral region of the epidural space such that the target tissue region is the posterior longitudinal ligament. In yet another example, positioning the neurostimulation lead within the patient may include positioning the neurostimulation lead between the spinal cord and a dura, such that the target tissue region is the spinal cord. In still another example, positioning the neurostimulation lead within the patient may include positioning the neurostimulation lead in a brain, such that the target tissue region is gray matter or white matter.

The method further includes measuring an impedance of each of the two electrodes; determining the difference between the impedances of the two electrodes; comparing the impedance difference to a threshold value; and re-positioning the neurostimulation lead relative to the target tissue region based on the comparison. Re-positioning the neurostimulation lead may include linearly displacing the neurostimulation lead closer to the target tissue region. In addition or alternatively, re-positioning the neurostimulation lead may include rotating the neurostimulation lead about the longitudinal axis to locate one of the electrodes closer to the target tissue region. The method may further include determining that the impedance difference is less than the threshold value. The method may further include affixing the neurostimulation lead after re-positioning the neurostimulation lead.

In accordance with a second aspect of the present inventions, a method for providing therapy to a patient is provided. The method includes measuring an impedance of each of the electrodes, and, based on the impedance measurement, selecting the electrode closest to the target tissue region. For example, the electrode having the lowest impedance may be selected to be the electrode closest to the target tissue region. In another example, the electrode having the highest impedance may be selected to be the electrode closest to the target tissue region. The method further includes conveying electrical stimulation energy from the selected electrode.

In one embodiment of the second aspect of the present inventions, the neurostimulation lead may be implanted within a ventral region of an epidural space of the patient, the target tissue region may be a posterior longitudinal ligament, and the electrode having the highest impedance may be selected to be the electrode closest to the posterior longitudinal ligament. In another embodiment of the second aspect of the present inventions, the neurostimulation lead may be implanted within an epidural space of the patient, the target tissue region may be a spinal cord, and the electrode having the lowest impedance may be selected to be the electrode closest to the spinal cord. In yet another embodiment of the second aspect of the present inventions, the neurostimulation lead may be implanted between a dura and a spinal cord, the target tissue region may be the spinal cord, and the electrode having the highest impedance may be selected to be the electrode closest to the spinal cord. In still another embodiment of the second aspect of the present inventions, the neurostimulation lead may be implanted within a brain of the patient with one of the electrodes adjacent to white matter and the other electrode adjacent to gray matter, and the target tissue region may be the white matter or the gray matter.

In accordance with a third aspect of the present inventions, a system for providing therapy to a patient is provided. The system includes an impedance monitor configured for being coupled to the electrodes and for measuring an impedance of each of the electrodes. The impedance monitor may be configured for continuously measuring the impedance of each of the electrodes. The system further includes a processor configured for determining a difference between the impedances of the electrodes, for comparing the difference to a threshold value, and for providing a suggestion to a user to re-position the neurostimulation lead within the patient based on the comparison. The suggestion may be to displace the neurostimulation lead closer to the target tissue region. In addition, or alternatively, the suggestion may be to rotate the neurostimulation lead about the longitudinal axis to locate one of the electrodes closer to the target tissue region. The target tissue region may be a spinal cord, a posterior longitudinal ligament, white matter, or gray matter. The processor may be configured to provide the suggestion to re-position the neurostimulation lead to the user only if the impedance difference is less than the threshold value.

In accordance with a fourth aspect of the present inventions, a system for providing therapy to a patient is provided. The system includes an impedance monitor configured for being coupled to the electrodes and for measuring an impedance of each of the electrodes, and a processor configured for, based on the impedance measurement, selecting the electrode closest to the target tissue region. The processor may be configured for selecting the electrode having the lowest impedance to be the electrode closest to the target tissue region. Alternatively, the processor may be configured for selecting the electrode having the highest impedance to be the electrode closest to the target tissue region. The system also includes a controller configured for instructing a neurostimulator to convey electrical stimulation energy from the selected electrode.

In one embodiment of the fourth aspect of the present inventions, the neurostimulation lead may be implanted within a ventral portion of an epidural space of the patient, the target tissue region may be a posterior longitudinal ligament, and the processor may be configured for selecting the electrode having the highest impedance to be the electrode closest to the posterior longitudinal ligament. In another embodiment of the fourth aspect of the present inventions, the neurostimulation lead may be implanted within an epidural space of the patient, the target tissue region may be a spinal cord of the patient, and the processor may be configured for selecting the electrode having the lowest impedance to be the electrode closest to the spinal cord. In yet another embodiment of the fourth aspect of the present inventions, the neurostimulation lead may be implanted within a brain of the patient with one of the electrodes adjacent to white matter and the other electrode adjacent to gray matter, and the target tissue region may be one of the white matter and the gray matter. In still another embodiment of the fourth aspect of the present inventions, the neurostimulation lead may be implanted between a spinal cord and a dura, the target tissue region may be the spinal cord, and the processor may be configured for selecting the electrode having the highest impedance to be the electrode closest to the spinal cord.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar neurostimulator, that may be used as a component of numerous different types of stimulation systems. The description that follows relates to a deep brain stimulation (DBS) system and a spinal cord stimulation (SCS) system. However, it is to be understood that the while the invention lends itself well to applications in DBS and SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a peripheral nerve stimulator, a microstimulator, or in any other neural stimulator configured to treat urinary incontinence, sleep apnea, shoulder sublaxation, headache, etc.

Figure 1:
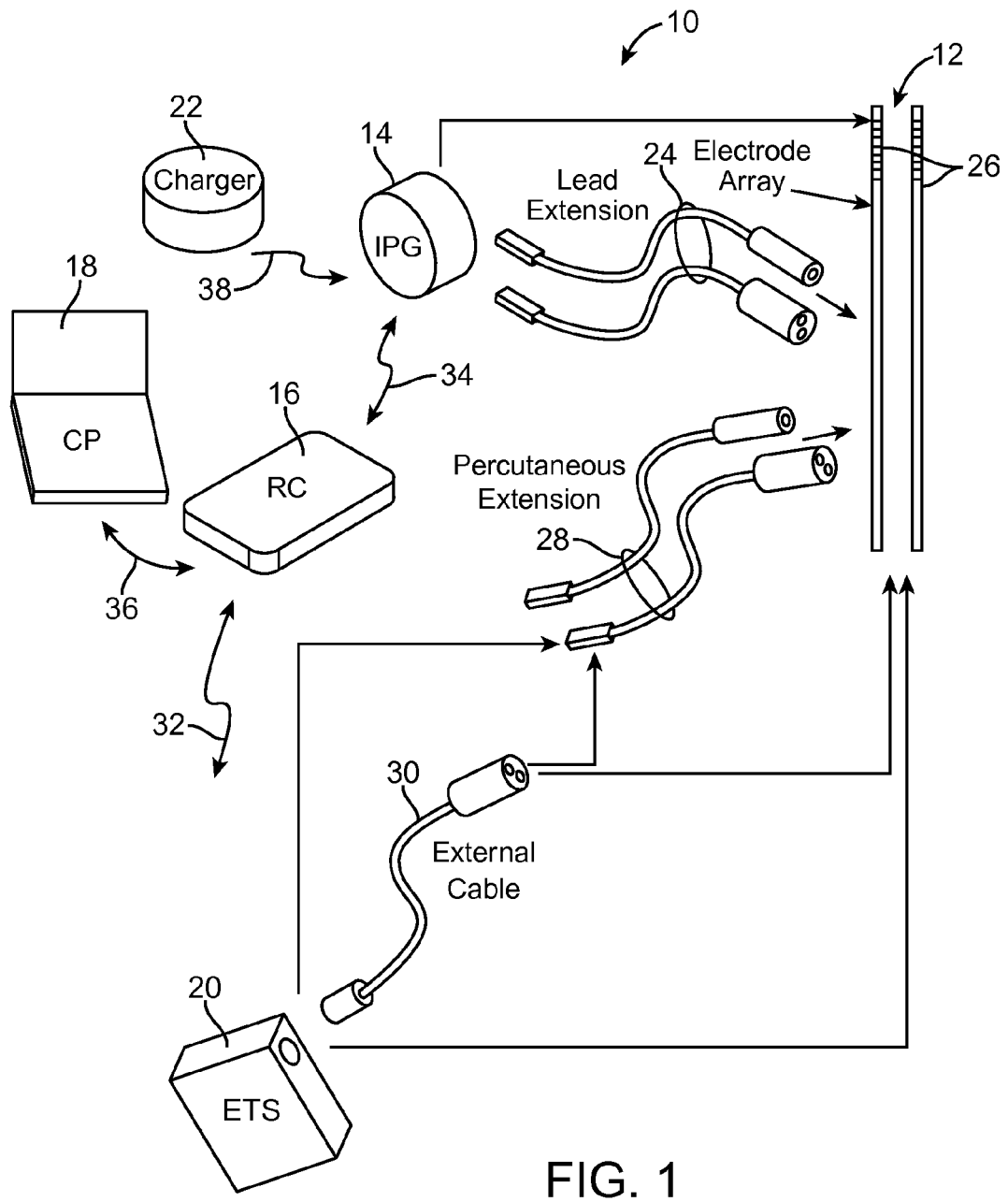
FIG. 1 is a plan view of an embodiment of a neurostimulation system arranged in accordance with the present inventions.

Turning first to FIG. 1, an exemplary neurostimulation system 10 generally includes at least one implantable neurostimulation lead 12 (in this case, two), a neurostimulator in the form of an implantable pulse generator (IPG) 14, a remote controller RC 16, a clinician's programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has pulse generation circuitry similar to that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used, on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
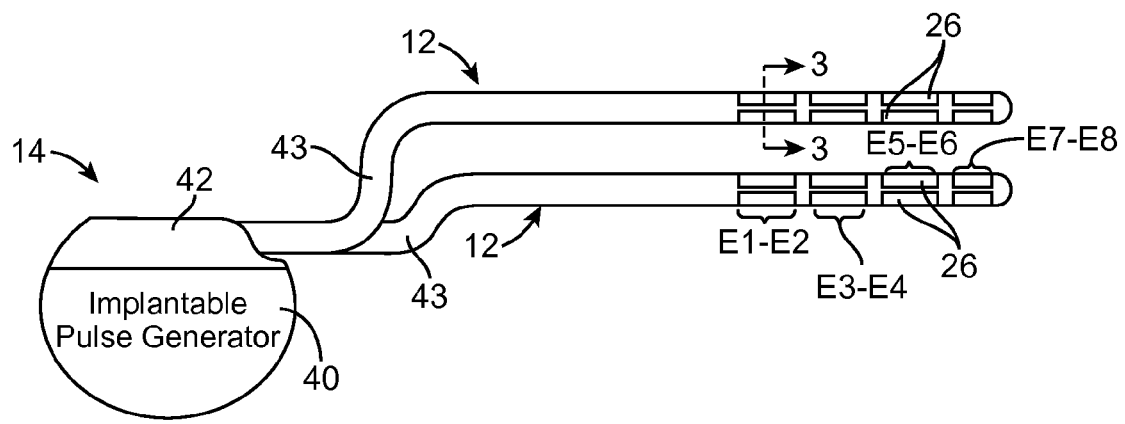
FIG. 2 is a profile view of an implantable pulse generator (IPG) and neurostimulation leads used in the neurostimulation system of FIG. 1.

Referring to FIG. 2, the IPG 14 comprises an outer case 40 for housing the electronic and other components, and a connector 42 to which the proximal end of the neurostimulation lead 12 mates in a manner that electrically couples the electrodes 26 to the internal electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Figure 3:
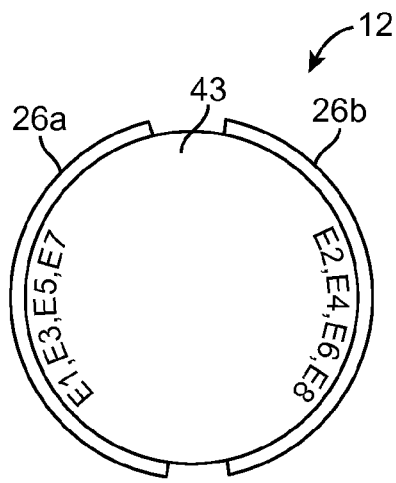
FIG. 3 is a cross-sectional view of a neurostimulation lead used in the neurostimulation system of FIG. 1.

Each of the neurostimulation leads 12 comprises an elongated cylindrical lead body 43, and the electrodes 26 take the form of segmented electrodes that are circumferentially and axially disposed about the lead body 43. By way of non-limiting example, and with further reference to FIG. 3, each neurostimulation lead 12 may carry eight electrodes, arranged as four rings of electrodes (the first ring consisting of electrodes E1 and E2; the second ring consisting of electrodes E3 and E4; the third ring consisting of electrodes E5 and E6; and the fourth ring consisting of electrodes E7 and E8) or two axial columns of electrodes (the first column consisting of electrodes E1, E3, E5, and E7; the second column consisting of electrodes E2, E4, E6, and E8). The two electrodes 26a, 26b in each electrode ring are diametrically disposed from each other. The actual number and shape of leads and electrodes will, of course, vary according to the intended application. For example, each ring of electrodes may include more than two electrodes. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

Figure 4:
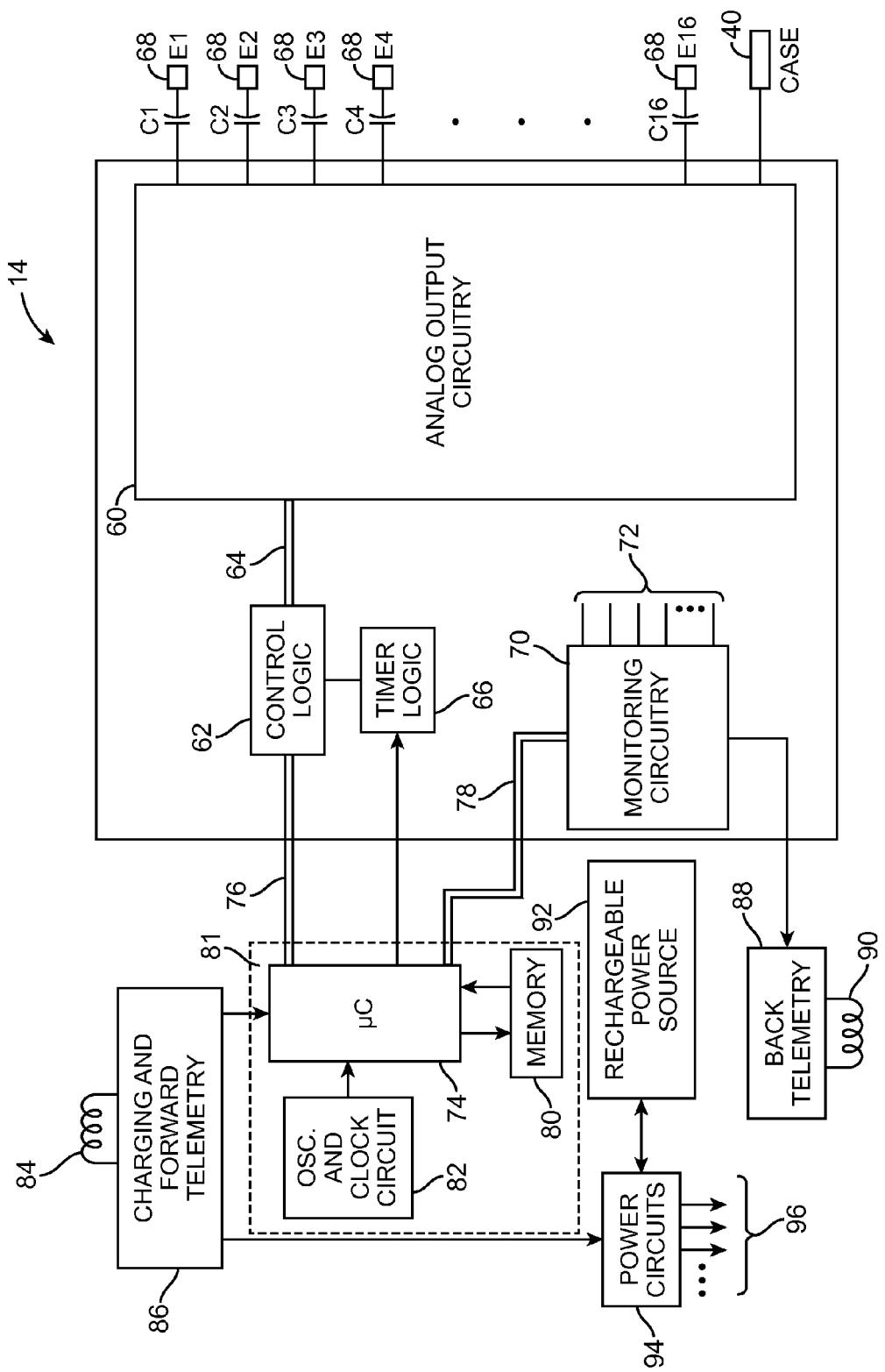
FIG. 4 is a block diagram of the internal components of the IPG of FIG. 1.

Turning next to FIG. 4, the main internal components of the IPG 14 will now be described. The IPG 14 includes stimulation output circuitry 60 configured for generating the electrical stimulation energy under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., battery voltage, temperature, and the like. Significantly, the monitoring circuitry 70 is configured for taking impedance measurements, so that, as will be described in further detail below, each of the leads 12 may be positioned correctly relative to a target tissue region and/or the electrode or electrodes closest to the target tissue region can be activated. The monitoring circuitry 70 may also measure the impedance at each electrode 26 in order to determine the coupling efficiency between the respective electrode 26 and the tissue and/or to facilitate fault detection with respect to the connection between the electrodes 26 and the analog output circuitry 60 of the IPG 14.

Impedance can be measured using any one of a variety means. For example, the impedance can be measured on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the impedance can be measured independently of the electrical stimulation pulses, such as described in U.S. Pat. Nos. 6,516,227 and 6,993,384, which were previously incorporated herein by reference.

To facilitate determination of the location of each neurostimulation lead 12, electrical signals can be transmitted between electrodes carried by one of the neurostimulation leads 12 and one or more other electrodes (e.g., electrodes on the same neurostimulation lead 12, electrodes on the other neurostimulation lead 12, the case 40 of the IPG 14, or an electrode affixed to the tissue), and then electrical impedance can be measured in response to the transmission of the electrical signals.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system 81 that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

Significantly, the microcontroller 74 is able to obtain impedance data from the monitoring circuitry 70. As discussed in more detail below, the microprocessor system 81 is configured for analyzing the impedance data in order to determine whether the neurostimulation lead 12 and the electrodes 26 are positioned correctly during implantation. The microprocessor system 81 may also be configured for providing a suggestion to a user to re-position the neurostimulation lead 12. In addition or alternatively, the microprocessor system 81 is configured for analyzing the impedance data in order to determine which of the electrodes 26 is closest to the target tissue region and for instructing the IPG 14 to convey electrical stimulation energy from that electrode. Alternatively or additionally, the CP 18 and/or the RC 16 may include processors and controllers for performing the tasks of obtaining the impedance data, analyzing the impedance data, determining whether the neurostimulation lead 12 and electrodes 26 are positioned correctly, providing a suggestion to a user to re-position the neurostimulation lead 12, determining which of the electrodes 26 is closest to the target tissue region, and instructing the IPG 14 to convey electrical stimulation energy from the electrode that is closest to the target tissue region.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (e.g., the impedance data) to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a replenishable power source 92, which may, e.g., comprise a rechargeable battery, such as a lithium-ion or lithium-ion polymer battery. The rechargeable battery 92 is recharged using rectified AC power (or DC power converted from AC power through other means, e.g., efficient AC-to-DC converter circuits) received by the AC receiving coil 84. To recharge the battery 92, the external charger 22, which generates the AC magnetic field, is placed against, or otherwise adjacent, to the patient's skin over the implanted IPG 14. The AC magnetic field emitted by the external charger 22 induces AC currents in the AC receiving coil 84. The charging and forward telemetry circuitry 86 rectifies the AC current to produce DC current, which is used to charge the battery 92.

The IPG 14 further comprises power circuits 94 to which the rechargeable battery 92 provides an unregulated voltage. The power circuits 94, in turn, generate the various voltages 96, some of which are regulated and some of which are not, as needed by the various circuits located within the IPG 14 for providing the operating power to the IPG 14. The power circuits 94 also include protection circuitry that protects the rechargeable battery 92 from overcharging. Also, safeguarding features are incorporated that assure that the battery 92 is always operated in a safe mode upon approaching a charge depletion. Potentially endangering failure modes are avoided and prevented through appropriate logic control that is hard-wired into the IPG 14, or otherwise set in the IPG 14 in such a way that the patient cannot override them.

Figure 5:
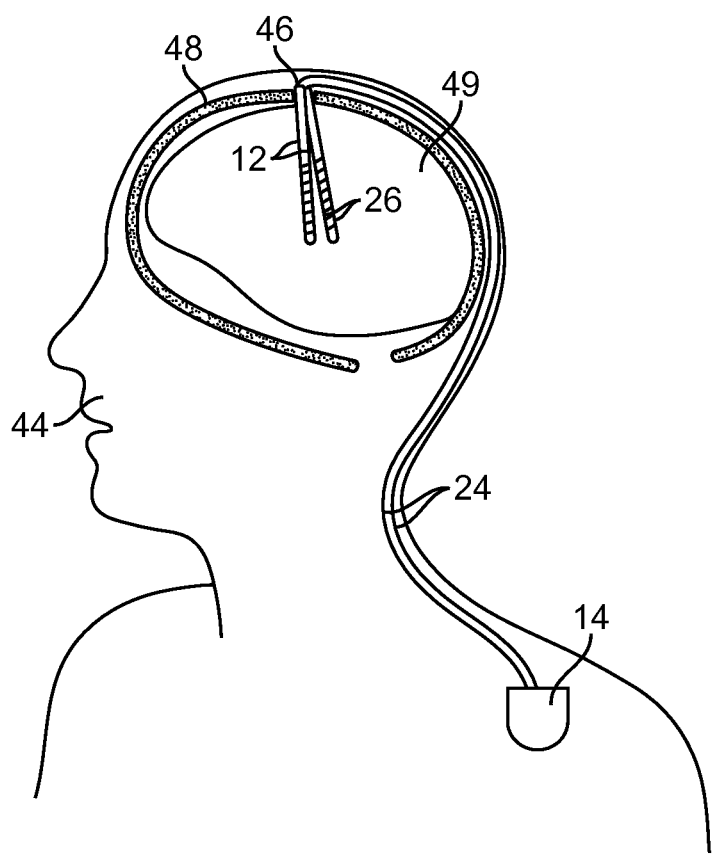
FIG. 5 is a plan view of the neurostimulation system of FIG. 1 in use within a patient in accordance with one embodiment of the present inventions.

The neurostimulation system 10 described above may be used for DBS or SCS. With DBS, as shown in FIG. 5, the two percutaneous neurostimulation leads 12 may be introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region. As discussed in more detail below, the target tissue region may be gray matter or white matter. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 6:
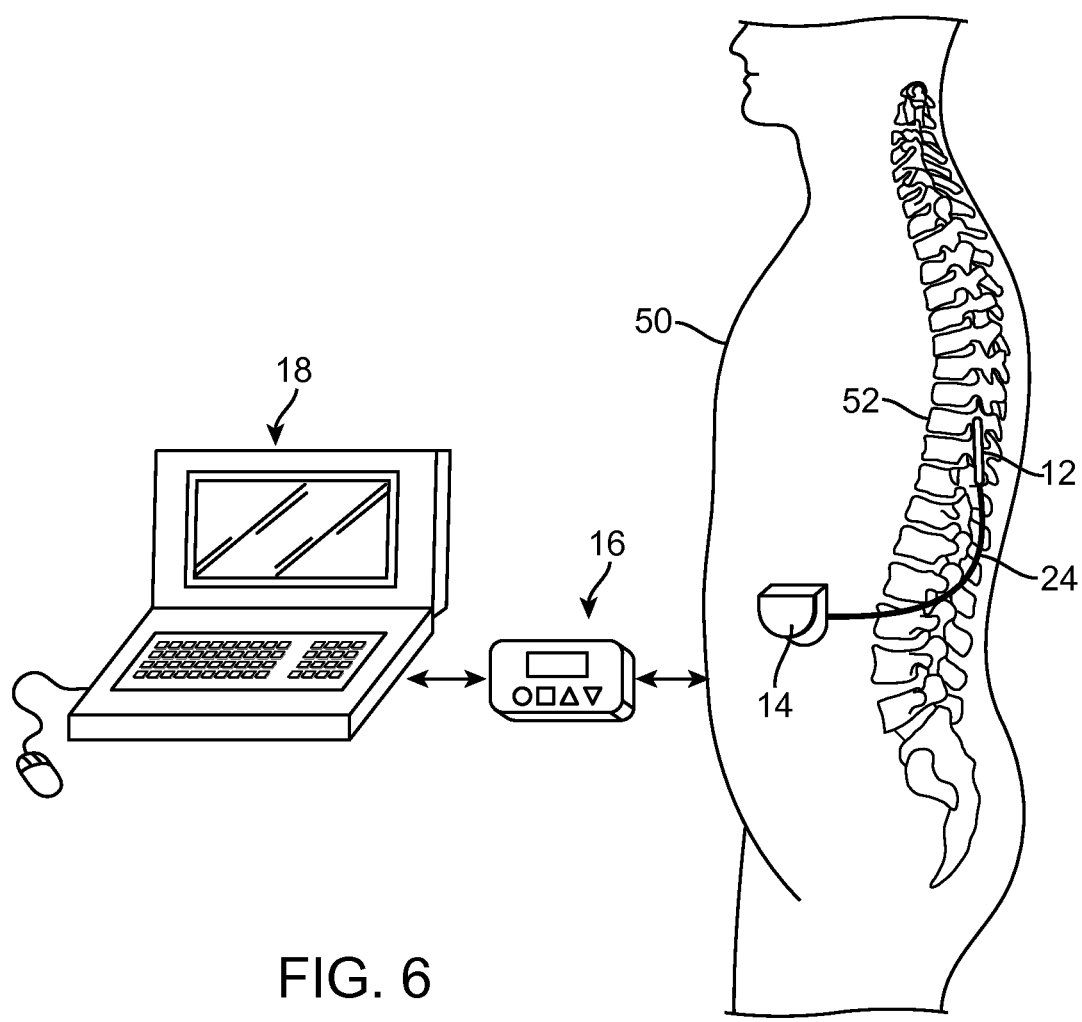
FIG. 6 is a plan view of the neurostimulation system of FIG. 1 in use within a patient in accordance with another embodiment of the present inventions.

With SCS, as shown in FIG. 6, the neurostimulation leads 12 are implanted within the spinal column 52 of a patient 50, such that the electrodes 26 are adjacent to target tissue. As discussed in more detail below, the target tissue in SCS may be, for example, the spinal cord or the posterior longitudinal ligament. Due to the lack of space near the location where the neurostimulation leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

As previously discussed, correctly placing the neurostimulation lead 12 near the target tissue is extremely difficult due to the limitations of imaging tools. In accordance with one embodiment of the present inventions, the impedance of each of the electrodes 26 is measured and the impedance measurement is used to determine whether the lead 12 is positioned correctly. Because different types of tissues have different conductive properties, by measuring the impedance at each electrode 26a, 26b, it is possible to determine whether the tissue adjacent to one of the electrodes 26a is different from the tissue adjacent to the other electrode 26b, and thus, whether the lead 12 is correctly positioned. As discussed in more detail below, a relatively large difference between the impedances of the electrodes 26a, 26b indicates that the lead 12 is correctly positioned, as shown in FIGS. 7A, 7D, 7E, and 7F. However, a relatively small difference between the impedances of the electrodes 26a, 26b indicates that the lead 12 is not correctly positioned, as shown in FIGS. 7B and 7C.

Figure 7A:
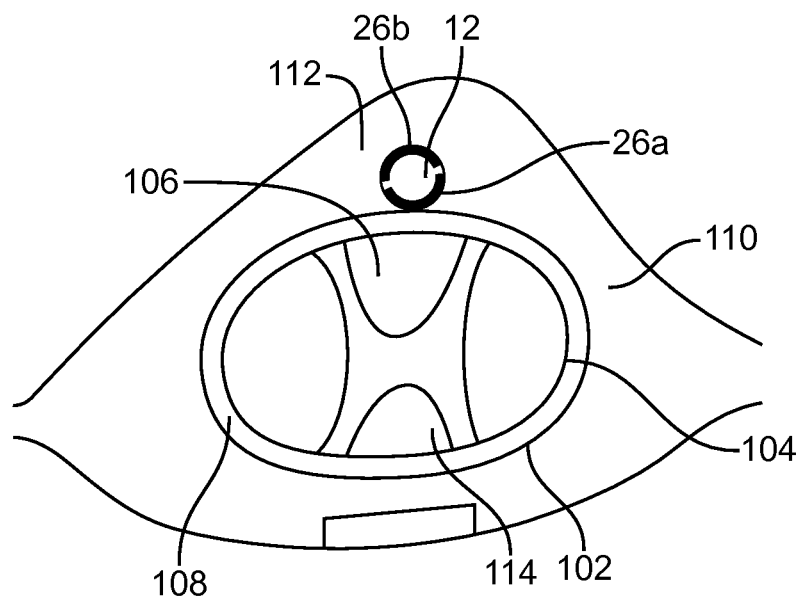
FIGS. 7A-7E are cross-sectional views of a spinal canal with a neurostimulation lead implanted therein in various positions.
Figure 7B:
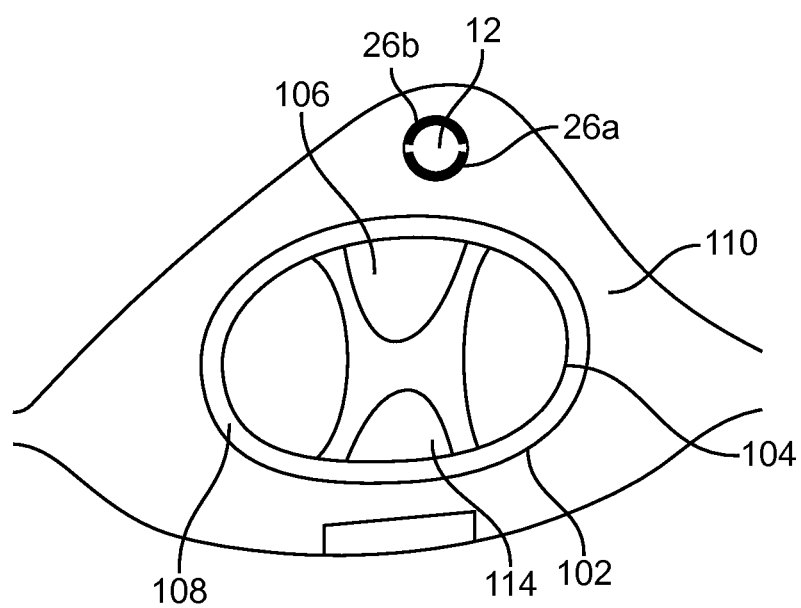
Figure 7C:
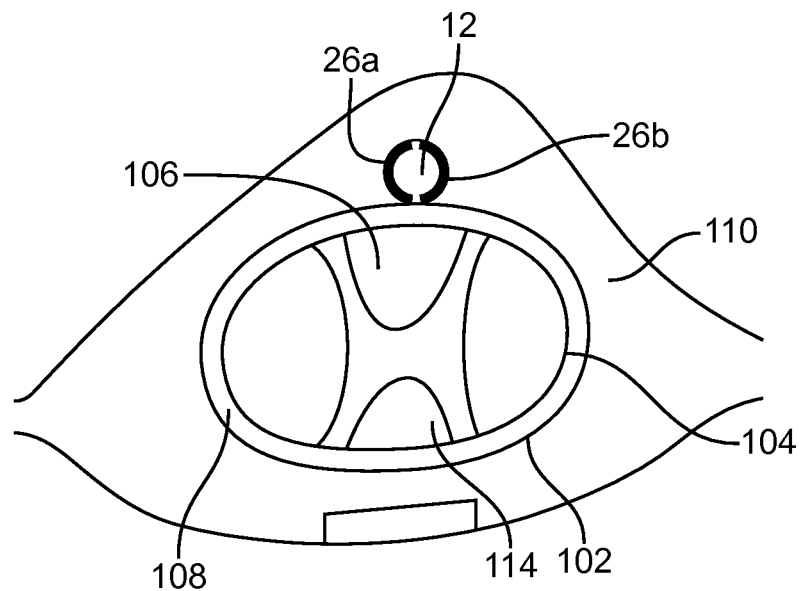

In the context of SCS, the embodiment shown in FIG. 7A takes advantage of the fact that the cerebrospinal fluid (CSF) 108 between the dura 102 and the spinal cord 104 is a good conductor, compared to the tissue in the epidural space 110, which is not a good conductor. In this embodiment, the target tissue region is the dorsal column 106 of the spinal cord 104, so the most preferred placement of the neurostimulation lead 12 is in the dorsal region 112 of the epidural space 110 with one of the electrodes 26a on the dura 102 of the spinal cord 104. With the lead 12 positioned as shown in FIG. 7A, the impedance of the electrode 26a in contact with the dura 102 is less than the impedance of the electrode 26b in the epidural space 110 because of the different conductive properties of the CSF 108 and the tissue in the epidural space 110. As such, the difference between the impedances of the electrodes 26a, 26b will be relatively large, indicating that the lead 12 is correctly positioned.

However, a relatively small difference between the impedances of the electrodes 26a, 26b indicates that the lead 12 is not in the correct position. For example, if the lead 12 is incorrectly positioned and is relatively medial between the dura and the inner boundary of the spinal canal ("floating in epidural space") 110, as shown in FIG. 7B, both of the electrodes 26a, 26b will have high impedances. In another example, shown in FIG. 7C, the location of the lead 12 may be correct, but the orientation of the lead 12 is incorrect. Since the electrodes 26a, 26b positioned as shown in FIGS. 7B and 7C will have similar impedances, the difference between the impedances of the electrodes will be small, indicating that the lead 12 is not correctly positioned.

It is advantageous to correctly position the lead 12 on the dura 102 during implantation, as shown in FIG. 7A, because after implantation, a capsule of fibrous cells and tissue will grow around the lead 12, thereby lifting the lead 12 off of the dura 102. Implanting the lead 12 as close to the dura 102 as possible ensures that, even after the growth of this fibrotic capsule, the electrodes 26a, 26b are still close enough to the dura 102 to be able to effectively apply stimulation to the dorsal column 106. Another advantage of correctly positioning the lead 12 is that unwanted stimulation of certain tissues near the epidural space 110 can be substantially avoided. Stimulation applied to the epidural space 110 may affect such tissues as the posterior ligamentum flavum, which is sometimes innervated with pain nerve fibers, resulting in an undesirable pinching sensation in the ligaments. In addition, it is undesirable to apply stimulation to the epidural space 110 because such stimulation would require high stimulation thresholds, and the stimulation field would not be very well-controlled.

Figure 7D:
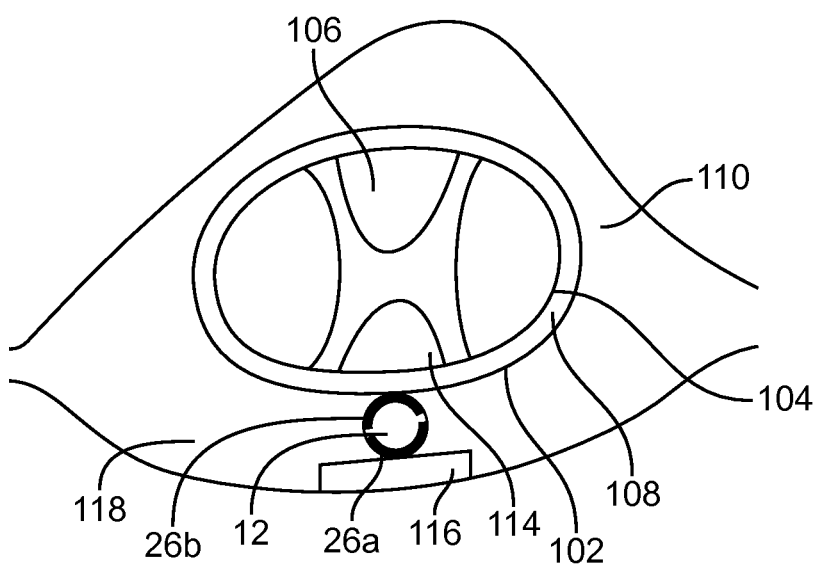

The embodiment shown in FIG. 7D takes advantage of the fact that the CSF 108 is more conductive than the posterior longitudinal ligament (PLL) 116. In this embodiment, the target tissue region may be the ventral column 114 and/or ventral roots of the spinal cord 104 or the PLL 116, so the neurostimulation lead 12 is implanted within the ventral region 118 of the epidural space 110 with one of the electrodes 26b facing the dura 102 of the spinal cord 104 and the other electrode 26a facing the PLL 116. Because of the difference in conductive properties between the CSF 108 and the PLL 116, the impedance of the electrode 26b facing the dura 102 is lower than the impedance of the electrode 26a facing the PLL 116. As such, the difference between the impedances of the electrodes 26a, 26b will be relatively large, indicating that the lead 12 is correctly positioned.

Figure 7E:
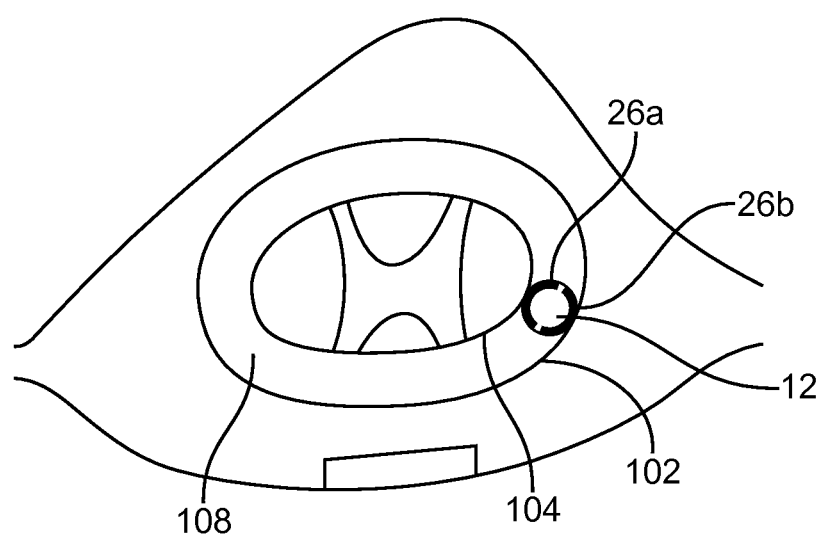

The embodiment shown in FIG. 7E takes advantage of the fact that the CSF 108 is more conductive than the spinal cord 104. In this embodiment, the target tissue region is the spinal cord 104, and the neurostimulation lead 12 is implanted subdurally between the spinal cord 104 and the dura 102 with one electrode 26a facing the spinal cord 104, and the other electrode 26b disposed within the CSF 108 and facing the inner surface of the dura 102. Because of the difference in conductive properties between the CSF 108 and the spinal cord 104, the electrode 26a facing the spinal cord 104 has a higher impedance than the electrode 26b disposed within the CSF 108. As such, the difference between the impedances of the electrodes 26a, 26b will be relatively large, indicating that the lead 12 is correctly positioned.

Figure 7F:
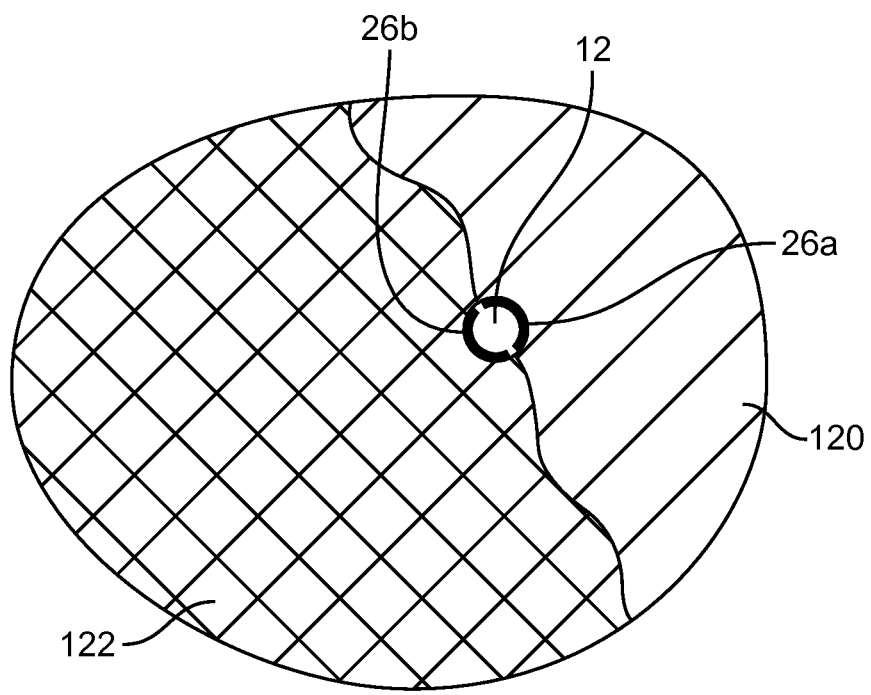
FIG. 7F is a cross-sectional view of a neurostimulation lead implanted within brain tissue.

In the context of DBS, the embodiment shown in FIG. 7F takes advantage of the fact that gray matter 122 is a better conductor than white matter 120. In this embodiment, the target tissue region may be the white matter 120 or the gray matter 122, so the neurostimulation lead 12 is implanted within the brain of the patient with one of the electrodes 26a facing the white matter 120 and the other electrode 26b facing the gray matter 122. Due to the differences in conductive properties between white matter 120 and gray matter 122, the electrode 26a disposed in the white matter 120 will have a higher impedance than the electrode 26b disposed in the gray matter 122. As such, the difference between the impedances of the electrodes 26a, 26b will be relatively large, indicating that the lead 12 is correctly positioned.

Figure 8:
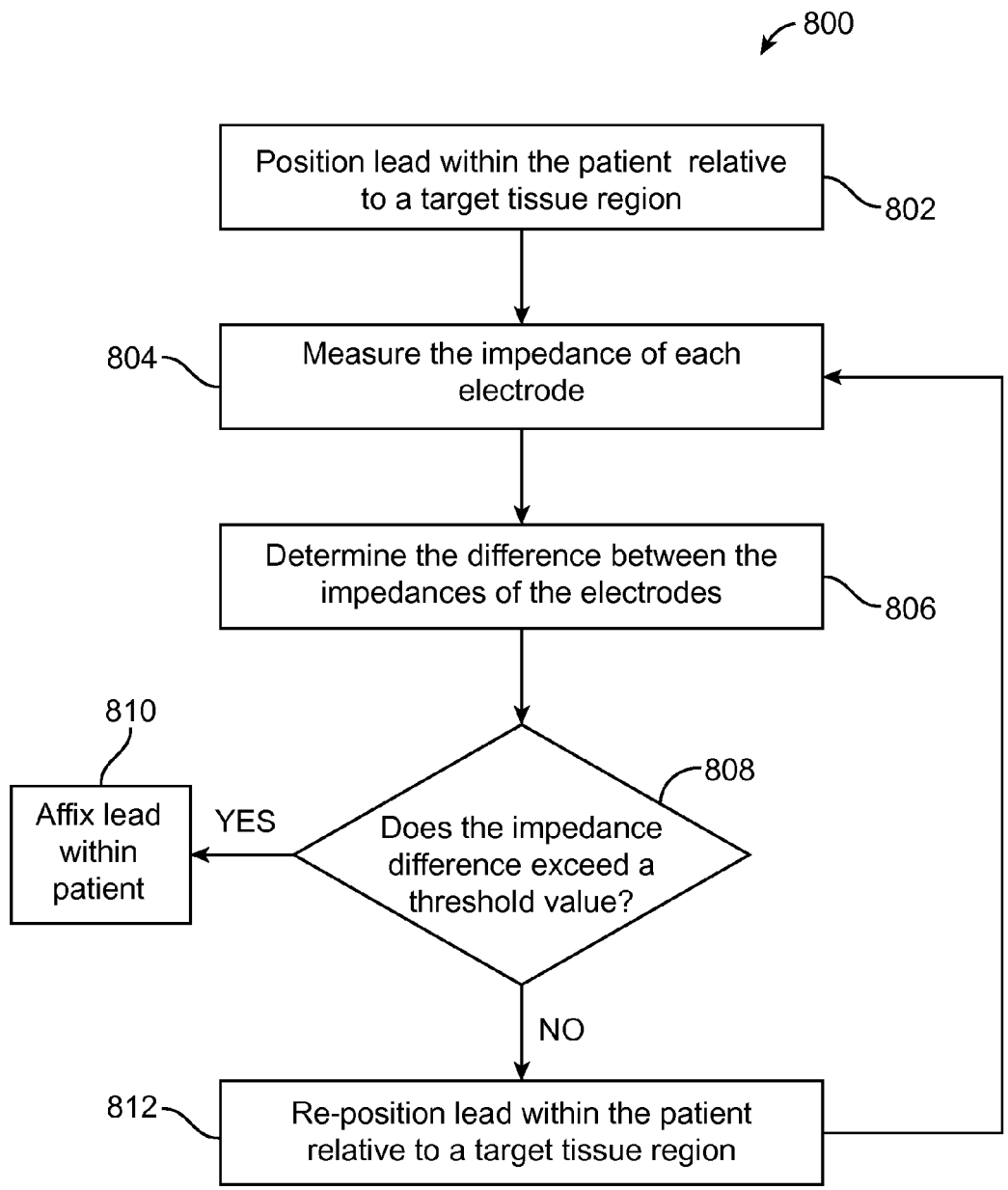
FIG. 8 is a flow chart illustrating a method of implanting a neurostimulation lead in accordance with one embodiment of the present inventions.

A method 800 for using impedance measurements to determine whether the lead 12 is correctly positioned is discussed with reference to FIG. 8. First, in step 802, the lead 12 is positioned within the patient relative to the target tissue region. Next, the impedance of each of the electrodes 26a, 26b is measured in step 804. The impedance may be continuously monitored during implantation. The difference between the impedances of the two electrodes 26a, 26b is then determined in step 806. Next, in step 808, the impedance difference is compared to a pre-determined threshold value. If the difference between the impedances exceeds the threshold value, indicating that the lead 12 is in the correct position (as discussed above), then the lead 12 is affixed (e.g., by suturing) within the patient in step 810. However, if the impedance difference does not exceed the threshold value, indicating that the lead 12 is not correctly positioned (as discussed above), then the processor 81 (see FIG. 4) is configured to provide a suggestion to the user to re-position the lead 12 in step 812. Re-positioning the lead 12 may include linearly displacing the lead 12 to be closer to the target tissue region, or may include rotating the lead 12. After re-positioning the lead 12, the impedances of the electrodes 26a, 26b are again measured (returning to step 804), an impedance difference is determined (step 806), the impedance difference is compared to a threshold value (step 808), and (if necessary), the lead 12 is again re-positioned (step 812). Steps 806, 808, and 812 may be repeated until it is determined in step 808 that the impedance difference exceeds the threshold value, and thus, that the lead 12 is correctly positioned.

One example of the method 800 will now be discussed with reference to FIGS. 7A-7C. In this example, the target tissue region is the dorsal column 106 of the spinal cord 104. Thus, in step 802, the lead 12 is positioned within the dorsal epidural space 112. If the lead 12 is correctly positioned, as shown in FIG. 7A, then it will be determined in step 808 that the difference between the impedances of the electrodes 26a, 26b exceeds the threshold value, and the lead 12 will be affixed within the patient in step 810. However, if the lead 12 is not correctly positioned, as shown in FIGS. 7B and 7C, then it will be determined in step 808 that the difference between the impedances does not exceed the threshold value, and the lead 12 will be re-positioned in step 812. For example, the lead 12 shown in FIG. 7B will be linearly displaced to be closer to the dorsal column 106, and the lead 12 shown in FIG. 7C will be rotated so that one of the electrodes 26a, 26b faces the dura 102.

Another example of the method 800 will be discussed with reference to FIG. 7D. In this example, the target tissue region is the ventral column 114 of the spinal cord 104, or the PLL 116. Thus, in step 802, the lead 12 is positioned with the ventral epidural space 118. If the lead 12 is correctly positioned, as shown in FIG. 7D, then it will be determined in step 808 that the difference between the impedances of the electrodes 26a, 26b exceeds the threshold value, and the lead 12 will be affixed within the patient in step 810. However, if the lead 12 is rotated or linearly displaced relative to the position depicted in FIG. 7D, then it will be determined in step 808 that the difference between the impedances does not exceed the threshold value, and the lead 12 will be re-positioned (e.g., linearly displaced or rotated) in step 812.

Another example of the method 800 will be discussed with reference to FIG. 7E. In this example, the target tissue region is the spinal cord 104. Thus, in step 802, the lead 12 is positioned subdurally between the dura 102 and the spinal cord 104. If the lead 12 is correctly positioned, as shown in FIG. 7E, then it will be determined in step 808 that the difference between the impedances of the electrodes 26a, 26b exceeds the threshold value, and the lead 12 will be affixed within the patient in step 810. However, if the lead 12 is rotated or linearly displaced relative to the position depicted in FIG. 7E, then it will be determined in step 808 that the difference between the impedances does not exceed the threshold value, and the lead 12 will be re-positioned (e.g., linearly displaced or rotated) in step 812.

Another example of the method 800 will be discussed with reference to FIG. 7F. In this example, the target tissue region may be the white matter 120 or the gray matter 122. Thus, in step 802, the lead 12 is positioned within brain tissue. If the lead 12 is correctly positioned, as shown in FIG. 7F, then it will be determined in step 808 that the difference between the impedances of the electrodes 26a, 26b exceeds the threshold value, and the lead 12 will be affixed within the patient in step 810. However, if the lead 12 is rotated or linearly displaced relative to the position depicted in FIG. 7F, then it will be determined in step 808 that the difference between the impedances does not exceed the threshold value, and the lead 12 will be re-positioned (e.g., linearly displaced or rotated) in step 812.

Figure 9:
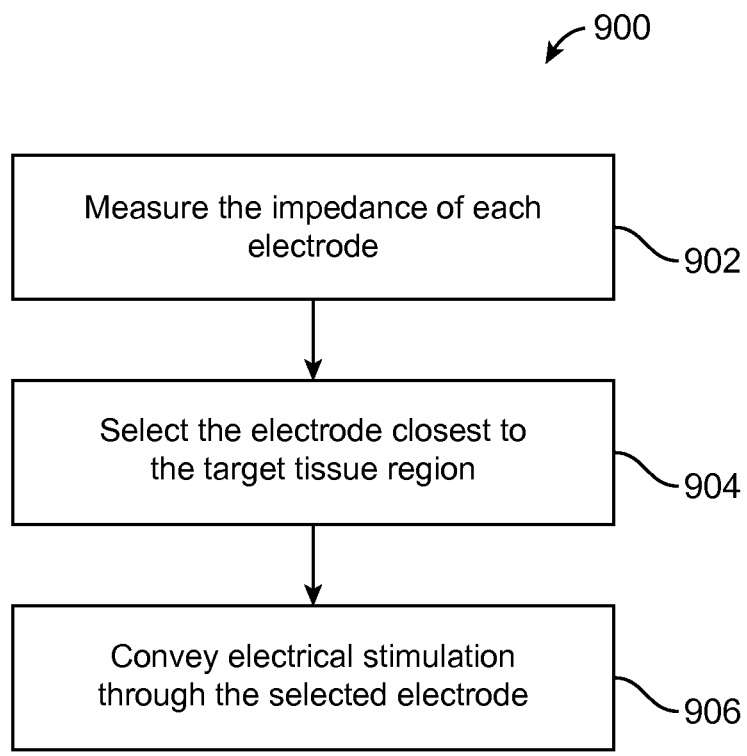
FIG. 9 is a flow chart illustrating a method of selecting one of the electrodes on the neurostimulation lead for conveying stimulation to the target tissue region.

A method 900 for using impedance measurements to determine which one of the electrodes 26a, 26b is closest to the target tissue region is discussed with reference to FIG. 9. First, in step 902, the impedance of each electrode is measured. Next, in step 904, the electrode closest to the target tissue region is selected. This selection in step 904 is based upon the impedance measurement. After the appropriate electrode is selected in step 904, electrical stimulation is conveyed through the selected electrode in step 906. In this manner, the electrical stimulation is directed predominantly at the target tissue region.

For example, referring back to FIG. 7A, the target tissue is the dorsal column 106 of the spinal cord 104. Thus, the electrode 26a closest to the dorsal column 106 is selected by measuring the impedances of the electrodes 26a, 26b and choosing the electrode 26a having the lowest impedance.

In another example, with reference to FIG. 7D, if the target tissue is the ventral column 114, then the electrode 26b closest to the ventral column 114 is selected by measuring the impedances of the electrodes 26a, 26b and choosing the electrode 26b having the lowest impedance. Alternatively, if the target tissue is the PLL 116, then the electrode 26a closest to the PLL 116 is selected by measuring the impedances of the electrodes 26a, 26b and choosing the electrode 26a having the highest impedance.

In yet another example, with reference to FIG. 7E, the target tissue is the spinal cord 104. Thus, the electrode 26a closest to the spinal cord 104 is selected by measuring the impedances of the electrodes 26a, 26b and choosing the electrode 26a having the highest impedance.

In still another example, with reference to FIG. 7F, if the target tissue is white matter 120, then the electrode 26a adjacent to the white matter 120 is selected by measuring the impedances of the electrodes 26a, 26b and choosing the electrode 26a having the highest impedance. Alternatively, if the target tissue is gray matter 122, then the electrode 26b adjacent to the gray matter 122 is selected by measuring the impedances of the electrodes 26a, 26b and choosing the electrode 26b having the lowest impedance.

In addition to, or instead of, measuring the impedance of each electrode 26a, 26b, the field potential of each electrode may be measured and used to determine whether the lead is correctly positioned and/or which of the electrodes is closest to the target tissue region. In general, field potential is a voltage potential measured at an electrode due to current flow within the region surrounding the electrode, the source of the current being from other electrodes i.e., the current does not come from the two electrodes where the voltage is being measured. Field potentials may be used instead of or in combination with the impedances and generally the same procedures may be applied as if impedances were used.

It should be noted that each ring of electrodes carried by the lead 12 may include more than two electrodes. By having more than two electrodes in each electrode ring, it may be easier to correctly position the lead 12 (e.g., it may be less likely that the lead will need to be rotated relative to the target tissue). In addition, more electrodes in each ring may result in greater control of the stimulation field, so that it is less likely that non-target tissue will be stimulated.

It should further be noted that the electrode selected to convey the electrical stimulation may change over time due, for example, to migration. Over time, if the lead 12 has rotated, then the processor is configured to use the impedance measurements to automatically adjust the current delivery towards the electrode with the closest value to the targeted tissue resistance. For example, a lead including three electrodes in each electrode ring is epidurally positioned to target the spinal cord (e.g., similar to the lead position shown in FIG. 7A), and a first electrode is initially determined to have the lowest impedance (suggesting it is closest to the dura and CSF). However, it may later be determined that a second electrode has a lower impedance. Thus, the processor may automatically adjust the current to be redirected to the second electrode.

Still further, it should be noted that current steering may be used to convey the electrical stimulation through two selected electrodes. For example, if a lead including three electrodes in each electrode ring is used, it may be determined that a first electrode and a second electrode both have lower impedances than a third electrode, but that impedance of the first electrode is slightly higher than that of the second electrode. In this case, the processor may be configured to employ current steering to direct fractional amounts of the total current in a mathematical relation to the impedance of the first and second electrodes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for providing therapy to a patient, the system for use with a neurostimulation lead positioned relative to a target tissue region having different conductive properties than other tissue proximate the neurostimulation lead, the neurostimulation lead having a longitudinal axis and an electrode ring segmented into two segmented electrodes circumferentially spaced from each other about the longitudinal axis, the system comprising:
   an impedance monitor configured for being coupled to the segmented electrodes and for measuring an impedance for each of the segmented electrodes to provide impedance data for each of the segmented electrodes, the impedance data for each of the segmented electrodes being dependent on conductive properties of tissue proximate to the segmented electrode;
   a processor configured for analyzing the impedance data for each of the segmented electrodes to select the segmented electrode from the two segmented electrodes of the electrode ring that is closest to the target tissue region; and
   a controller configured for instructing a neurostimulator to convey electrical stimulation energy from the selected segmented electrode.

2. The system of claim 1, wherein the processor is configured for selecting the segmented electrode that is closest to the target tissue region by selecting the segmented electrode from the two segmented electrodes of the electrode ring that has a lower impedance.

3. The system of claim 1, wherein the processor is configured for selecting the segmented electrode that is closest to the target tissue region by selecting the segmented electrode from the two segmented electrodes of the electrode ring that has a higher impedance.

4. The system of claim 1, wherein the neurostimulation lead is implanted within a ventral portion of an epidural space of the patient, wherein the target tissue region is a posterior longitudinal ligament, and wherein the processor is configured for selecting the segmented electrode that is closer to the posterior longitudinal ligament by selecting the segmented electrode from the two segmented electrodes of the electrode ring that has a higher impedance.

5. The system of claim 1, wherein the neurostimulation lead is implanted within an epidural space of the patient, wherein the target tissue region is a spinal cord of the patient, and wherein the processor is configured for selecting the segmented electrode that is closer to the spinal cord by selecting the segmented electrode from the two segmented electrodes of the electrode ring that has a lower impedance.

6. The system of claim 1, wherein the neurostimulation lead is implanted within a brain of the patient with one of the segmented electrodes of the electrode ring adjacent to white matter and the other segmented electrode of the electrode ring adjacent to gray matter, and-wherein the target tissue region is one of the white matter and the gray matter.

7. The system of claim 1, wherein the neurostimulation lead is implanted between a spinal cord and a dura, wherein the target tissue region is the spinal cord, and wherein the processor is configured for selecting the electrode closest to the spinal cord by selecting the segmented electrode in the electrode ring that has the higher impedance.

8. A system for providing therapy to a patient, the system for use with a neurostimulator and with a neurostimulation lead positioned relative to a target tissue region having different conductive properties than other tissue proximate the neurostimulation lead, the neurostimulation lead having a longitudinal axis and a circumference, and at least two segmented electrodes circumferentially spaced from each other around the circumference of the lead such that one of the segmented electrodes is closest to the target tissue region, the system comprising:
   an impedance monitor configured to be operably connected to the neurostimulation lead to perform an impedance measurement for each of the segmented electrodes to provide impedance data for each of the segmented electrodes, the impedance data for each of the segmented electrodes being dependent on conductive properties of tissue proximate to the segmented electrode;
   a processor configured to compare the impedance data to identify and select the segmented electrode closest to the target tissue region; and
   a controller configured to instruct the neurostimulator to deliver electrical stimulation energy to the target tissue region using the selected segmented electrode.

9. The system of claim 8, wherein the targeted tissue region has a higher conductivity than tissue surrounding the targeted tissue region, and the processor is configured to compare the impedance measurements to determine which of the at least two segmented electrodes has a lowest impedance measurement in order to select the segmented electrode closest to the target tissue region.

10. The system of claim 9, wherein the neurostimulation lead is within an epidural space of the patient, and the target tissue region is a spinal cord of the patient.

11. The system of claim 9, wherein the target tissue region is gray matter.

12. The system of claim 8, wherein the targeted tissue region has a lower conductivity than tissue surrounding the targeted tissue region, and the processor is configured to compare the impedance measurements to determine which of the at least two segmented electrodes has a highest impedance measurement in order to select the segmented electrode closest to the target tissue region.

13. The system of claim 12, wherein the target tissue region is a posterior longitudinal ligament.

14. The system of claim 12, wherein the target tissue region is white matter.

15. The system of claim 12, wherein the neurostimulation lead is between a spinal cord and a dura, wherein the target tissue region is the spinal cord.

16. A system, comprising:
a neurostimulation lead positioned relative to a target tissue region having different conductive properties than other tissue proximate the neurostimulation lead, the neurostimulation lead having a longitudinal axis and a circumference, and at least two segmented electrodes circumferentially spaced from each other around the circumference of the lead;
an impedance monitor configured to be operably connected to the neurostimulation lead to perform an impedance measurement for each of the segmented electrodes to provide impedance data for each of the segmented electrodes, the impedance data for each of the segmented electrodes being dependent on conductive properties of tissue proximate to the segmented electrode;
a processor configured to compare the impedance data to identify and select a segmented electrode closest to the target tissue region;
a neurostimulator configured to be operably connected the neurostimulation lead; and
a controller configured to instruct the neurostimulator to deliver electrical stimulation energy to the target tissue region using the selected segmented electrode.

17. The system of claim 16, wherein the targeted tissue region has a higher conductivity than tissue surrounding the targeted tissue region, and the processor is configured to compare the impedance measurements to determine which of the at least two segmented electrodes has a lowest impedance measurement in order to select the segmented electrode closest to the target tissue region.

18. The system of claim 17, wherein the neurostimulation lead is within an epidural space of the patient, and the target tissue region is a spinal cord of the patient.

19. The system of claim 17, wherein the target tissue region is gray matter.

20. The system of claim 16, wherein the targeted tissue region has a lower conductivity than tissue surrounding the targeted tissue region, and the processor is configured to compare the impedance measurements to determine which of the at least two segmented electrodes has a highest impedance measurement in order to select the segmented electrode closest to the target tissue region.

21. The system of claim 20, wherein the target tissue region is a posterior longitudinal ligament.

22. The system of claim 20, wherein the target tissue region is white matter.

23. The system of claim 20, wherein the neurostimulation lead is between a spinal cord and a dura, wherein the target tissue region is the spinal cord.

* * * * *